United States Patent [19]

Coleman et al.

[11] 4,356,317

[45] Oct. 26, 1982

[54] ACYLOXYALKENOIC ACIDS AND PROCESS THEREFOR

[75] Inventors: James P. Coleman; Richard C. Hallcher, both of Maryland Heights; Dudley E. McMackins, St. Charles, all of Mo.

[73] Assignee: Monsanto Company, St. Louis, Mo.

[21] Appl. No.: 222,200

[22] Filed: Jan. 2, 1981

[51] Int. Cl.³ .............................................. C07C 67/05
[52] U.S. Cl. ................................... 560/241; 549/326; 424/311
[58] Field of Search ................ 560/241, 244, 246, 247

[56] References Cited

U.S. PATENT DOCUMENTS

| | | | |
|---|---|---|---|
| 3,346,622 | 10/1967 | Selwitz | 560/241 |
| 3,927,077 | 11/1975 | Finkbeiner | 560/241 |
| 3,992,417 | 11/1976 | Dessau | 260/343.6 |
| 4,044,041 | 8/1977 | Stapp | 560/241 |
| 4,100,362 | 7/1978 | Stapp | 560/246 |
| 4,175,089 | 11/1979 | Heiba | 260/343.6 |

FOREIGN PATENT DOCUMENTS

| | | | |
|---|---|---|---|
| 52-39612 | 3/1977 | Japan | 560/246 |
| 1138366 | 1/1969 | United Kingdom | 560/244 |

OTHER PUBLICATIONS

Uemura, J., Chem. Soc., D, pp. 1630–1631 (1970).

*Primary Examiner*—Michael L. Shippen
*Attorney, Agent, or Firm*—Joseph D. Kennedy; James W. Williams, Jr.

[57] ABSTRACT

Acyloxyhexenoic acids are produced by reaction of butadiene and acetic acid with metal salt oxidants in a process involving electrolytic regeneration of the metal oxidants during the reaction.

27 Claims, 1 Drawing Figure

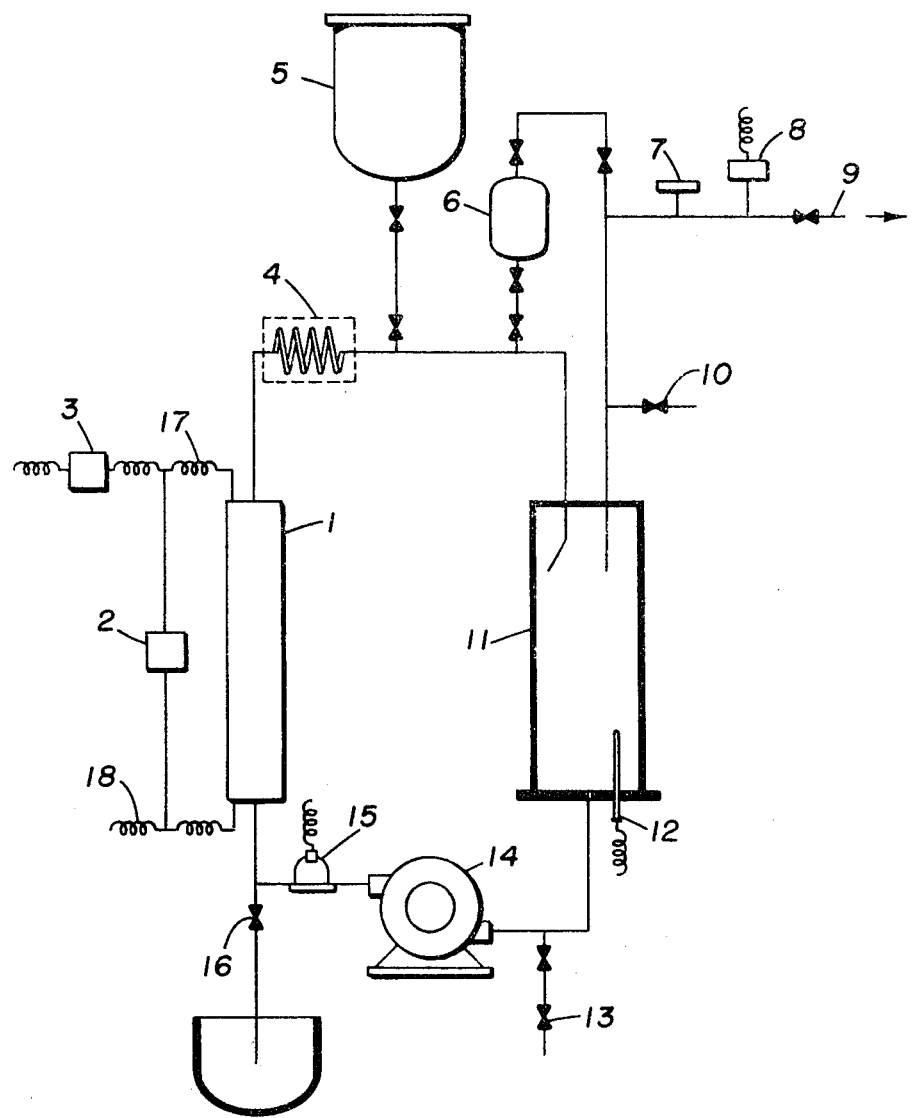

ACYLOXYALKENOIC ACIDS AND PROCESS THEREFOR

The present invention relates to a method of producing acyloxyhexenoic acids from the reaction of butadiene and carboxylic acids in the presence of metal salt oxidants. In particular, the method involves the electrolytic regeneration of the metal ion oxidant during the reaction in the presence of the reactants and products, and recovery of acyloxyhexenoic acid products.

BACKGROUND OF THE INVENTION

Procedures are known for reacting butadiene and acetic acid in the presence of stoichiometric amounts of trivalent manganese components to produce γ-vinyl-γ-butyrolactone. Such procedures could involve the use of large amounts of manganese with consequent problems for large scale processes in handling large amounts of poorly soluble metal salts in reaction mixtures.

SUMMARY OF THE INVENTION

The present invention is exemplified by the reaction of butadiene, acetic acid, acetic anhydride and metal salt oxidant to produce acetoxy hexenoic acids, with use of less than stoichiometric metal salt oxidant and electrolytic regeneration thereof in the reaction mixture with re-use as the reaction occurs. In the reaction process, conditions, particularly the presence of acetic anhydride, are such as to facilitate production of acetoxyhexenoic acids rather than lactone products. In one particular aspect copper ions are utilized along with another metal oxidant to improve selectivity to the acetoxyhexenoic acids. In another aspect, use of carbon or similar anodes contributes to obtaining the desired reaction.

DETAILED DISCLOSURE

The present invention in its preferred exemplification involves the reaction of butadiene and acetic acid to produce the isomeric compounds, 6-acetoxy-4-hexenoic acid and 4-acetoxy-5-hexenoic acid. With manganic acetate as the metal salt, the reaction can be represented

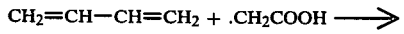

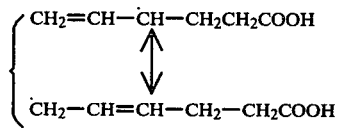

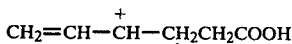

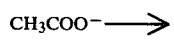

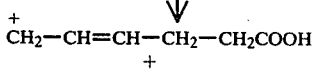

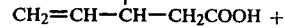

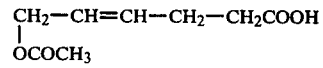

The overall reaction is

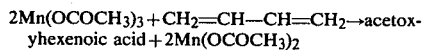

In the present invention the manganese acetate is oxidized by electrolysis during the overall reaction and the resulting manganic acetate utilized to effect reaction of acetic acid and additional butadiene as the reaction continues.

The present invention involves the reaction of butadiene and alkanoic acid in the presence of a metal ion oxidant. The metal ion can be various reducible metal salts or other compounds, particularly manganese, vanadium or cerium salts in higher valent form. The metal will have a valence higher than the lowest valence above the zero valent form. In the discussion hereinbelow manganese will generally be used as illustrative of such metals, and in fact is oridinarily preferred. While the manganese can be supplied in various forms, it will preferably be in the trivalent state for the reaction.

It is important to the present invention that the trivalent manganese can be readily regenerated electrolytically in the presence of the other reaction components and products. For the overall reaction, two moles of manganese are needed for each mole of butadiene. However, the facile regeneration makes it feasible to employ only a small proportion of manganese in the reaction, e.g. about 0.1 mole per mole of butadiene, or about 5% of stoichiometric amount. It is advantageous to work with small amounts of manganese, e.g. 5% or less by weight of the reaction mixture, in order to avoid or minimize problems in handling reaction mixtures containing large amounts of poorly soluble salts. It has been found feasible to conduct the electrolysis during the reaction in the presence of various reaction components, despite the possibility of competing reactions at the anode or cathode. Among such possible reactions are reduction or polymerization of butadiene at the cathode and plating out of manganese at the cathode. It is also possible to have anodic initiated polymerizations, or to oxidize butadiene to diacetoxy compounds at the anode. However, despite the foregoing it has been found advantageous to use less than stoichiometric amounts of manganese and to electrolytically regenerate trivalent manganese during a reaction to form acetoxyhexenoic acids from butadiene and acetic acid.

With olefins other than butadiene, conditions similar to those of the present process can produce a variety of products, including unsaturated acids, saturated acids, lactones and telomers. The present reaction, involving a diolefin, presents possibilities of reactions different from those with monoolefins. It has been found that the reaction can be directed toward the 6-acetoxy-4-hexenoic and 4-acetoxy-5-hexenoic acids. This is advantageous, as it has further been found that these isomeric acids can be readily converted to sorbic acid. It is fortunate that the acetoxyhexenoic acids are produced, rather than a hexadienoic acid, as the latter could react with the metals in the reaction mixture and present a difficult separation problem and product loss.

It has been found that the presence of copper ion greatly improves the selectivity of the reaction to the desired acetoxyhexenoic acids. It is believed that the present reaction involves formation of a carboxymethyl radical from acetic acid, which then adds to butadiene forming a radical adduct; and that the latter is then oxidized to a carbonium ion. Apparently the copper ion is instrumental in accelerating the conversion to a carbonium ion, and, fortunately does not interfere by similarly oxidizing the carboxymethyl radical at an earlier stage. The oxidation of the radical adduct is helpful in directing the reaction toward the desired acetoxyacids, and avoiding telomerization, oligomerization or similar reactions of the radical adduct. The copper also appears to be effective in some way in accelerating the reaction of trivalent manganese, thereby lessening the concentration of trivalent manganese and lessening the amount of its reduction at the cathode, with consequent improvement in current efficiency. The applicants are not to be bound to a particular mechanism, as the copper ions are beneficial and effective in improving selectivity to the desired acetoxyacids and efficiency of the electrolytic process, regardless of what the mechanism may be.

Copper ions are, of course, known to be electrolitically oxidizable and reducible. The copper in bivalent form can act as an oxidant, and it is believed this is the primary mode in which copper is effective in the present process. In acting as an oxidant, the copper is reduced to monovalent copper, and this is regenerated at the anode to bivalent copper, whether directly or by reaction with trivalent manganese Thus the electrolysis is useful in effecting regeneration of the bivalent copper, as well as the trivalent manganese. However, the use of copper in the electrolysis system does present some difficulties. Copper is reduced at the cathode and has a tendency to plate out on the cathode. As the cathode becomes plated with copper, there is an increasing loss of butadiene by reduction to butene at the cathode. Various procedures can be adapted to lessen the copper deposition or otherwise minimize the butadiene reduction.

As apparent from the discussion of the present invention, a number of different reactions are occurring in the present process. Consequently, for purposes of control it is desirable to regulate certain parameters so that the various reactions will occur in desirable ratios. The electrochemical conversion of divalent manganese to trivalent manganese occurs readily, and accordingly, the size of the electrodes, or the dwell time for electrolysis in a continuous system, can be kept relatively low. Correspondingly, a reservoir can be kept in the reactor for the chemical reaction to be completed. The concentration of divalent manganese in the vicinity of the anode can advantageously be relatively high in order to minimize oxidative attack on the butadiene or acetate ion. A fairly high concentration of butadiene provides availability to react with the carboxymethyl radicals generated in the process. Fairly high concentrations of butadiene are particularly advantageous when copper salts are utilized along with the manganese salts. There is a marked improvement in selectivity to acetoxyhexenoic acids, due to the copper, under such conditions. This is important since the higher butadiene concentrations are also preferred for the improved reaction rates. In the absence of copper, high butadiene concentration may increase production of side products. Such concentrations of butadiene will generally be greater than about 0.25 mole per liter, and often greater than about 1 mole per liter, and many range up to about 5 mole or more per liter, or possibly to solubility limits under the reaction conditions, with pressure being necessary to obtain the higher solubilities.

The present process is suitably conducted under mild temperature and pressure conditions. Atmospheric pressures can be utilized, but it may be found useful to utilize pressures slightly in excess of atmospheric to increase the solubility of butadiene in reaction media. Still higher pressures can be employed, but such are unnecessary and involve additional expense. Elevated temperatures are useful in increasing speed of the reaction, but relatively mild temperatures are generally sufficient, such as in the range of about 60° to about 120° C. Higher temperatures can be employed, but as the temperature is increased, there is a greater tendency toward production of polymers of butadiene, as well as a possible need for pressurized vesels. The acetoxyhexenoic acids are still reasonably stable at temperatures up to 140° C. or 160° C. and on up to 250° C. of so in the presence of acetate salts, and particularly in the presence of acetic anhydride.

The present invention involves production of a product which has moieties found in butadiene and acetic acid. However, acetic anhydride is advantageously utilized in the process along with acetic acid, and it may be that either the carboxymethyl or acetoxy moieties of the product come from the acetic anhydride. Also, the acetic components may come from manganese triacetate, rather than directly from acetic acid. Even so the present reaction can be characterized as a reaction of butadiene and acetic acid, and such reaction as used herein includes all of the foregoing variations in reaction components.

The acetoxyhexenoic acids are produced in good yield in the process. The acids are formed and present in the reaction mixture along with the butadiene, acetic acid and acetic anhydride components of the mixture, and the metal components of the mixture. The acetoxyacids are separated from the reaction mixture to have a product suitable for conversion to sorbic acid. However, a complete separation is not necessary as a crude acetoxyhexenoic acid can be converted to sorbic acid. It will generally be desirable to effect a fairly complete separation from the metal components, and this is further appropriate in order to recycle the metal ions to the reaction. The acetic acid can be present during the conversion to sorbic acid. Even so it may be found convenient to separate part or all of these components as an aid to effecting separation from the metal salts, or in order to recycle the components to the reactor. It will generally be desirable to remove the butadiene component for recycle. In a laboratory procedure, butadiene and acetic acid can be stripped off under reduced pressure with heating, and the residue partitioned between ether and water, with the acetoxyacids being found in the ether and the metal salts in the water. The ether can then be flashed off and the residue utilized for conversion to sorbic acid. In a procedure potentially suitable for large scale operations, the volatile butadiene and part of the acetic can be flashed off, and then an organic solvent added to dissolve the acetoxyhexenoic acids, and filtration under pressure can be utilized for separation from the precipitated metal salts. It is not necessary to distill the acetoxyhexenoic acids from higher boiling material prior to conversion to sorbic acids. Also, substantial amounts of acetic acid or other solvents can be present during the conversion, and in fact, it is generally desirable to have a solvent present during the conversion.

In effecting the present process, it is almost a requirement to have acetic anhydride present along with the acetic acid and butadiene reactants. The acetic anhydride has a very significant effect on the rate of the reaction, and in fact the reaction rate is generally very poor in the absence of acetic anhydride. However, it is also desirable to have substantial amounts of acetic acid present, as the acetic acid provides better salt solubility than acetic anhydride. Aside from solubility and reactivity aspects of the reaction medium, it is desirable to have conductivity sufficient to avoid unnecessarily high electrical resistance with attendant energy costs. The amounts of acetic anhydride when present can vary considerably, but will usually be in the range of about 0.1 to about 5 moles per mole of acetic acid, and preferably in the range of about 0.2 to about 0.8 moles per mole of acetic acid, although amounts up to about 1.5 moles per mole of acetic acid can be used with fairly good results. In addition to affecting the reaction rate, the acetic anhydride affects the reaction by directing it toward the acetoxyacids, rather than lactone. In the absence of the anhydride, there may be water present in the reaction mixture from the addition of hydrated manganese salts. The acetoxyacids are prone to hydrolysis in the presence of water, and the resulting hydroxyacids can cyclize to the lactone. However if acetic anhydride is present, it serves to take up the available water, forming acetic acid. Thus the acetic anhydride serves to stabilize the acetoxyhexenoic acid products. The acetic anhydride may contribute further to the formation and stabilization of the acetoxyhexenoic acids, by means other than involved in taking up water. It appears that other means of avoiding the presence of water, or drying the reaction mixture, could be substituted for the use of acetic anhydride, and the reaction could then produce acetoxyhexenoic acids in the absence of acetic anhydride. Thus the process can desirably be conducted in the absence of water or under virtually anhydrous conditions. However, the acetic anhydride has a beneficial effect on reaction rate and is also very convenient for use, and alternate procedures may compare unfavorably. Other acid anhydrides can, if desired, be substituted for acetic anhydride, although there is generally no advantage in such substitution. For example, alkanoic acid anhydrides, particularly those of lower alkanoic acids can be used, as can benzoic acid anhydride. Such anhydrides may result in some replacement of acetoxy groups by other acyloxy groups or otherwise contribute to obtaining a mixture of products.

Solvents can be utilized in the present process to attain solubility of the reaction components in the reaction mixture. As acetic acid is a reasonably good solvent, the use of solvents other than the reaction components is ordinarily unnecessary. However, other solvents can be employed if desired. Other carboxylic acids can be employed, although such acids tend to interfere by competing with acetic acid in the reaction suitability will depend upon relative reaction rates and the amount of side product which is acceptable. For electrolytic efficiency, it is preferred to use polar solvents or other solvents of relatively good electrical conductivity such as acetic acid.

The manganese ion utilized for effecting oxidation in the present process is primarily trivalent manganese, but the manganese can be supplied to the reaction in practically any form capable of forming manganese ions in the reaction mixture. If the manganese is supplied in divalent form, it is converted to trivalent manganese by electrolysis for reaction in the process. If provided in a higher than trivalent form, it can initially react as an oxidant in such form and subsequently be regenerated by electrolysis as trivalent manganese for further reaction in the process. The manganese can conveniently be supplied as manganic acetate dihydrate, anhydrous manganic acetate, or as a mixture of manganese dioxide and acetic acid.

Cerium has two positive valence states, 3 and 4, and can be conveniently supplied in the higher valence state as ceric acetate. It can also be supplied in any other form capable of forming ions in the reaction mixture, and oxidized to the tetravalent state if necessary by electrolysis.

Vanadium has three positive valence states, 2, 3 and 5, and can conveniently be supplied in the higher valent vanadic forms as the acetate. It can also be supplied in any other forms capable of forming ions in the reaction mixture, and oxidized to the tri- or pentavalent state by electrolysis.

The electrolysis for regeneration of higher valent metal can be conducted in an electrolysis cell comprising a container or vessel with electrodes. The desired oxidation of the metal ion occurs at the anode, and it is advantageous to utilize an anode material facilitating this oxidation. Carbon anodes have been found suitable, particularly porous carbon as such unfilled carbon electrodes give better results than pitch-impregnated graphite. High surface area carbon anodes are especially useful, as contributing to effectiveness of high current usage without significant loss in product selectivity. Various carbon fiber or particulate carbon electrodes are known to the art and can be used with advantage, such as carbon cloth and carbon felt electrodes. Some such materials have very high reported surface areas, such as 32.5 square meters per square centimeter of geometric surface, although a lesser part of such surface area would be contacted by an electrolyte. Other anode materials of high oxygen over potential are suitable in theory, but it happens that platinum tends to cause ready polymerization of butadiene, making it impractical for use unless at very low current densities, or possibly in some high surface area configuration. Moreover, the manganese containing reaction medium is highly corrosive and tends to dissolve or corrode many potential electrode materials under electrolysis conditions. Dimensionally stable metal oxide or alloy electrode materials may be suitable as anodes, as well as gold or some other noble metals. In essence the anode is one which is suitable for effecting oxidation of manganous ion in the presence of acetic acid and butadiene, which may eliminate materials with an undue propensity to effect polymerization of butadiene in such environment. The anode, as well as the cathode if it contacts the manganese containing medium, will preferably be resistant to corrosion by the medium.

High surface area electrodes will preferably have many times that surface area calculated from the planar dimensions assuming a flat, planar surface, such as 10 times such area, or advantageously 100 or more times such surface area. The actual effective surface area is uncertain, but calculations can be made assuming a penetration into a fiber or similar electrode of 0.2 mm. or so. The cathode is essentially a counter electrode in the cell to complete the electric circuit and does not effect a reaction essential to the process. Conventional electrode materials can be employed as cathode, including various carbons, metals and alloys. However, the cathode can still affect the process with regard to electrical efficiency and side reactions. The cathode reaction would preferably be limited to reduction of hydrogen ion with generation of hydrogen, but is likely to involve some reduction of metal ion or other components of the reaction mixture. For example, trivalent manganese can be reduced to divalent manganese, and copper can be reduced to the metal with plating out on the cathode. Also butadiene can be reduced to butene at the cathode. To some extent, the cathode material will affect these undesirable reductions. Carbon cathodes, particularly, graphite, have been found convenient for use. The undesirable cathode reactions can also be lessened by various techniques of cell or electrode design, or by control of relative concentrations of components. For example, a divided cell can be employed in which the electrodes are separated by a semi-permeable membrane and only particular ions are permitted to migrate across the membrane. Or the cathode can be covered by a porous membrane to lessen contact of the reaction medium with the cathode. The concentrations of various components and electrolysis current can be selected with a view to having a relatively high concentration of acetic acid near the cathode, compared to the butadiene concentration there.

The electrolysis cell will utilize the reaction mixture as the electrolysis medium. It will be understood, of course, that in a continuous process the reaction mixture will change with time and extent of reaction, product separation, recycle of various components and introduction of additional increments of components. For large scale operations it is contemplated that the cell will have electrodes of relatively large area which are separated by a relatively short distance, and that the reaction mixture will be circulated between the electrodes. The electrolytic regeneration of the trivalent manganese will be taking place at the same time as the reaction utilizing the trivalent manganese in the production of acetoxyhexenoic acids. Both the electrolytic and chemical parts of the reaction can be conducted in an electrolysis cell between the electrodes. However, as the rates of the reaction may differ, it is preferable to have part of the reaction mixture in an electrolysis cell and part of it in an additional chamber or portion of the same chamber. The chambers can then be sized and the circulation rate between the electrodes regulated so as to obtain suitable sojurn times without unnecessarily large electrode areas. The trivalent manganese will be regenerated to an extent suitable for the chemical reaction being recirculated between the electrodes at a rate suitable for this purpose, and the reaction mixture will be held in the reaction chambers for a time sufficient to obtain the desired degree of conversion to acetoxyhexenoic acids. The process is capable of achieving high conversions, such as better than 95% based on butadiene. Since acetic acid is often used in large excess, the conversions on acetic will generally be lower. Since butadiene can be recycled, it may at times be preferred to have less than maximum conversion in a continuous process, balancing needs for suitability of reaction rate and product selectivity with suitable conversion. In a continuous process a product stream can be taken off at a rate to permit the desired conversion. Aside from recycle of reactants and electrolyte after separation from product, a stream or portion of the reaction mixture will be continuously circulating between the electrodes of the electrolysis cell.

As noted hereinabove, over some concentration ranges the butadiene concentration affects the rate of the reaction. Recognizing this, there may still be advantage at times in use of low butadiene concentrations. Thus, in a circulating system, if the butadiene has substantially reacted before circulating between electrodes, the butadiene at low concentration will be less subject to reaction or other interfering reactions at the electrodes. Also, if copper ions are not utilized, low butadiene concentrations may contribute to selectivity to acetoxyhexenoic acid products, e.g. such concentrations as those in the range of 0.05 to 0.3 mole per liter, or ranges generally lower than about 0.25 mole per liter, and used with modest manganese concentrations, e.g. 0.12 mole per liter, but even so in fairly high ratio to the butadiene. In some cases the amount of manganese may approach or even exceed stoichiometric with respect to the butadiene, but not present a particular handling problem as the concentrations on a weight basis are still low. Low butadiene concentrations can substantially avoid cathode reduction without need for a divided cell or other protection from the cathode.

In addition to metal salt oxidants, it is desirable to have other salts present in the reaction mixture to improve conductivity. Alkali metal salts are among those suitable, and it is convenient to utilize alkali metal acetates, e.g. sodium or potassium acetates, in order to avoid the unnecessary presence of anions other than acetate. Moreover the alkali metal acetates, particularly potassium acetate, appear to contribute to selectivity to and stability of the desired acetoxyhexenoic acid products. Various other electrolyte salts can be used if desired.

In large scale electrolytic operation there is advantage in having electrodes separated by only a narrow gap, with electrolysis medium flowing between the electrodes, and a reservoir to hold the balance of the electrolysis medium. A convenient flow electrolysis system is illustrated in the FIGURE.

The electrolysis cell 1 has electric leads 17 and 18 across which voltmeter 2 is connected and with ammeter 3 in lead 17. The exit line from the top of the cell has an optional heat exchanger 4, and inlets for solvent electrolyte charge from vessel 5 and butadiene from cylinder 6 and leads into reservoir 11. Rupture disc 7, strain gauge 8, vent 9 and gas sample valve 10 are also provided. The reservoir has thermocouple 12 for temperature measurement. The exit line from the reservoir has a valve for liquid sampling at 13 and leads to pump 14 for cycling through orifice -D.P. Cell 15 for flow measurement and into cell 1, and is also provided with a drain valve for draining at 16. The electrolysis cell 1 contains two parallel carbon electrodes (not illustrated) separated by a one-eighth inch polytetrafluoroethylene gasket, with entry and exit plenums (not illustrated) so that the electrolysis medium can flow between the electrodes. The various procedures described herein for producing acetoxyhexenoic acids can, if desired, be adapted to use in the illustrated flow electrolysis system.

In a process employing electrolysis, as described herein, the capital costs of electrolytic cells will be a very important factor in the overall costs of the process and the resulting product. Accordingly, it is important to have high productivity from the cells, as by operating the cells at reasonably high current densities. Of course the high current density should be accompanied by good current efficiency and selectivity to desired product. In order to obtain good results at high current densities in the present process, it is necessary to have good transport of the appropriate metal ions to the anode for oxidation, and appropriate vessels and time available for the reaction with the oxidized metal ions. For example, employing current density of 100 milliamperes/cm$^2$ or greater, and manganese concentration of about 100 millimoles per liter, the reaction medium can be circulated suitably through a small volume electrolysis cell at a rate to provide cycling the entire reaction medium in a short time, e.g. if volume of the reaction mixture is 1 liter, it can be circulated at possibly 1 liter per minute or better through an electrolysis cell with anode chamber capacity (opposite effective electrode surface) of 10–15 ml or so and effective anode area (apparent) of 40–50 cm$^2$ or so. The concentration and transport of $Mn^{+2}$ should be such that sufficient $Mn^{+2}$ is available at the anode to support the current. It is also necessary to provide sufficient butadiene to form desired product through the oxidations effected by the manganic ions which are generated. The required reactions can for the most part occur outside the cell in a reservoir which will generally be of many times greater capacity than the electrolysis cell. With sufficient acetic acid and butadiene being available for oxidation and further reaction, the manganese may for the most part be in divalent or other than trivalent state. When copper ion is present, the butadiene can be varied over fairly wide ranges without affecting results greatly. For example, butadiene might be present at 100 millimoles per liter and manganese similarly at 100 millimoles per liter, but with only 20–25 millimoles on the average present as $Mn^{+3}$. However, there may be advantage in having fairly high concentrations of butadiene to insure sufficient butadiene for high reaction rates, employing several times the trivalent manganese on a molar basis. The manganese concentrations will generally be in the range of about 10 to about 300 millimoles per liter, when copper is also utilized, and the trivalent form might be regenerated at a rate to provide concentrations of at least about 1 millimole per liter, but more likely about 10 to about 50 millimoles per liter, with the butadiene provided to be in a range on a molar basis of 3 or 4 up to about 10 times that of the trivalent manganese. About 50 to about 150 or so millimoles butadiene per liter may be convenient, particularly if such concentrations are obtainable by solubility of butadiene at atmospheric pressure. If higher temperatures and elevated pressures are employed, it may be advantageous to employ higher concentrations of butadiene in view of the faster reaction at elevated temperatures, and the feasibility of higher concentrations under elevated pressure conditions.

In view of the capital and other costs associated with electrolysis cells, it is desirable that a process employing electrolysis have a high production rate such as about 0.25 gram mole of acetoxy acids per liter-hour and advantageously production rates of as much as 1 gram mole per liter hour. Fortunately it has been found in the present invention that the process can be conducted under high reaction rate conditions, over 0.1 gram mole of acetoxyhexenoic acids per liter hour, utilizing high current densities and fairly high concentrations of reactants, with retention of good selectivity to desired products, such as better than 70% or possibly better than 80 or 90%, whether calculated on current efficiency to acetoxyhexenoic acids, or on butadiene reacted to such product. Despite the series of reactions involved in producing the desired product, and the possibility of alternate or interfering reactions, electro-initiated and chemical, it has been found that the process can be conducted efficiently at high rates and with high current densities. It has been found that the process can be operated at high conversion rates without substantial polymerization of the butadiene and with good selectivity to product, based on butadiene. By providing for continuous discharge of a product stream, as well as continuous addition of butadiene and acetic acid, it is feasible to operate the process as a continuous process with the concentrations of butadiene, manganese, trivalent manganese, etc., as well as acetoxy hexenoic acid product, reaching a steady state and being maintained at appropriate levels within the ranges described herein.

The surface area of the electrode can have a great influence on the reaction. For example, use of a high surface area anode material makes good results attainable at high current densities with flow rates and concentrations which would not otherwise be appropriate for high current density operation. Good results with carbon felt anodes at current densities over 100 milliamperes/cm$^2$ can be obtained at linear flow-rates of 10 to 20 cm/second, and possibly even lower. The current densities referred to are nominal, calculated on the area of the anode measured as a flat surface. For a flat planar carbon anode, with limited or minimal porosity, good results at current densities over 100 milliamperes/cm$^2$ may require flow rates over 200 cm/second and rates as high as 400 cm/second may be advantageous. There is definite advantage in use of high flow rates with high current densities, particularly if low surface area anodes are used. The referred-to flow rates are with respect to flow parallel to an anode, and through a small gap between electrodes, or between the anode and a membrane, such as a gap of 3.2 mm ($\frac{1}{8}$ inch) between an anode and a membrane separator, and appropriate flow rates may vary with respect to the particular type of flow and distance between electrodes. Use of turbulence promoters may be advantageous and permit use of lower flow rates calculated on a volume basis, while true flow rates over portions of the anode surface are faster than the calculated rate. The appropriate flow rates will also vary with the manganese ion concentration, particularly the divalent manganese concentration, being inversely related thereto. Thus in ranges of say 100 to 300 millimoles manganese per liter, for high production rates, there is considerable variation in the flow-rates needed for effective operation at high current density.

The operation of the present process at current density appropriate for the mass transfer conditions is particularly important since improper conditions, in addition to causing poor product selectivity, can cause polymerization and electrode fouling and even make is necessary to shut down the operation. With appropriate conditions, long term operations are possible with very little electrode fouling.

The following examples are illustrative of the invention.

EXAMPLE 1

A 600 ml. glass-lined pressure reactor equipped with a dip tube, thermocouple and pressure gauge, was modified to contain electrodes. The area of the graphite electrodes exposed to the reaction medium was 31.6 cm$^2$ and the electrode separation was 3.1 cm. A porous polytetrafluoroethylene membrane covered the cathode. The cell was charged with acetic acid, 110 ml., acetic anhydride 110 ml., sodium acetate, 25 grams, manganous acetate tetrahydrate, 12.5 grams, and 27 grams butadiene. Electrolysis and reaction was carried out at 0.5 ampere for 9.4 hours while the temperature was maintained at 95°–97° C. The pressure increased from 56 to 76 psig, and the applied voltage (to maintain constant current) increased from 18.5 to 23.5. The reaction mixture was stirred by continuously pumping head gas through a sparge tube between the electrodes. At the end of the alloted reaction time, the reaction mixture was heated to evaporate volatiles and the residue was partitioned with diethyl ether and water to effect separation of organic products and salts. The ether was evaporated from the ether layer, leaving crude acetoxyhexenoic acids. Determination of acetoxyacids was accomplished by vapor phase chromatographic analysis of a silylated sample of the crude product, using ethyl myristate as standard. Analysis showed 3.4 grams of acetoxyacids for a current efficiency of 22.5% to this product. The acetoxyacids were identified as 6-acetoxy-4-hexenoic acid and 4-acetoxy-5-hexenoic acid by comparison with an analysis of previously identified samples of these acids, obtained in a similar procedure.

A dip tube sample of the reaction mixture had been taken at the end of the reaction time, and this was analyzed for butenes by vapor phase chromatography, using hexane as an internal standard. The amount of butene was 0.74 gram, for a current efficiency of 15%.

EXAMPLE 2

The cell of Example 1 was charged with 147 ml acetic acid, 73 ml acetic anhydride, 25 grams sodium acetate, 12.5 grams manganous acetate tetrahydrate, 3.7 grams cupric acetate monohydrate, and 28.4 grams butadiene. The cathode was covered by a porous polytetrafluoroethylene membrane. Reaction with electrolysis was carried out at 1 ampere current of 6.25 hours, with a decrease in voltage from 35 to 32 volts, and increase in pressure from 74 to 126 psig. Product separation and analyses were carried out as in Example 1, showing 17.3 grams of acetoxyhexenoic acids, for a 73% current efficiency, and 5.7 grams butenes, for an 83% current efficiency.

EXAMPLE 3

A reaction was carried out utilizing reaction mixture components as in Example 2, but without a membrane on the cathode. A 0.5 ampere current was maintained for 21.4 hours as voltage fell from 14 to 12 volts and pressure increased from 80 to 86 psig. Analysis showed 11.4 grams of acetoxyhexenoic acids.

EXAMPLE 4

Heating in the presence of an acidic catalyst was employed to convert acetoxyhexenoic acids to sorbic acid. An 0.8 gram amount of a mixture of 4-acetoxy-5-hexenoic acid and 6-acetoxy-4-hexenoic acid in 5 ml. 1,4-dioxane was heated to reflux in the presence of 1.5 gram of an acidic ion exchange resin, Amberlyst ® 15, for 5 hours. The yield of sorbic acid was 85%.

EXAMPLE 5

A 0.8 gram amount of the crude mixture of acetoxyhexenoic acids from Example 3 in 5 ml. glacial acetic acid was heated at reflux in the presence of the Amberlyst ® acidic resin for 1.5 hours to give a 79% yield of sorbic acid.

EXAMPLE 6

A cell was used like that of Example 1, but stirring was accomplished by continuous liquid circulation through the cell. The cell was charged with 160 ml. acetic acid, 40 ml. acetic anhydride, 30 grams potassium acetate, 12.5 grams Mn(acetate)$_2$.4H$_2$O, 1 gram Cu(acetate)$_2$.H$_2$O, and 11.3 grams butadiene. A Nafion ®, sulfonated fluoroether polymer, membrane covered the cathode and was above the liquid level in the cell. Electrolysis was carried out at 105°–110° C. at 0.75 ampere, during which time the voltage increased from 8.5 to 26.5 volts. The reactor was vented to 120 psi gauge when the pressure exceeded 150 psi gauge. Analysis showed 18.3 grams acetoxyhexenoic acids, for a current efficiency of 80%, 0.336 gram butenes, for a current efficiency of 4.5%, and 2.79 grams of unreacted butadiene. The selectivity to acetoxyhexenoic acids based on reacted butadiene was 67.6%.

EXAMPLE 7

A procedure was carried out as in Example 6 but with the liquid level in the cell above the level of the Nafion ® membrane. The butadiene charge was 18.8 grams. After 10 hours at 1 ampere, analysis showed 22.1 grams of acetoxyhexenoic acids, current efficiency of 68.8%, and 1.92 grams of butenes for current efficiency of 18.4%. With 6.99 grams of unreacted butadiene, the selectivity to acetoxyhexenoic acids was 58.7%.

The use of a Nafion ® or similar membrane as described herein protects the cathode from butadiene and particular ions, thereby affecting the reactions which occur there. The membrane is intended to prevent the transport of copper and manganese ions because of their size, but to permit transport of potassium ion solvated with acetic acid. The reactions can be represented:

| | |
|---|---|
| ANODE | $Mn^{+2} - e \longrightarrow Mn^{+3}$ |
| MEMBRANE TRANSPORT | $K^+$ HOAC |
| CATHODE | $K^+ + HOAC + e \longrightarrow$ |
| | $KOAC + \frac{1}{2}H_2$ |
| OVERFLOW | $KOAC + HOAC$ |

As the reaction continues, potassium acetate and acetic acid build up between the membrane and the cathode, and material eventually overflows the top of the membrane to join the main part of the electrolyte on the anode side of the membrane. Even so, the system has the advantage of restricting access of the butadiene to the cathode, thereby lessening its reduction to butene. In another embodiment, the cathode was covered with a membrane, but with provision for exit of material from behind the membrane, as described in the following example.

EXAMPLE 8

A cell was utilized with two graphite electrodes 30 mm. by 50 mm, and separated by a 3.2 mm gap with provision for circulating electrolyte horizontally through the gap. The cathode was loosely covered by a Nafion ® 120 membrane which was closed on the upstream side, but open on the downstream side where electrolyte solution exited from the cell, extending about 50 mm beyond the cathode. A solution of Mn $(acetate)_2.4H_2O$, 7 grams, potassium acetate, 16.9 grams, $Cu(acetate)_2.H_2O$, 2.1 grams, 77 ml. acetic acid, 37 ml. acetic anhydride and 16.6 grams butadiene was recirculated between the electrodes. A current of 0.5 ampere was passed for 9 hours. Temperature of the solution was 108° C. Analysis of the product mixture showed 9 grams of acetoxyhexenoic acids, for a current efficiency of 62% to this product. The current efficiency to butene was 15%.

A divided electrochemical cell was utilized for a number of procedures as described in examples hereinbelow. The plate-and-frame divided electrochemical cell was constructed of stainless-steel back-plates with Teflon ® gaskets used to form the anolyte and catholyte passages. Anode and cathode surfaces were 6 cm × 15 cm with inlets at each end of the longer dimension. Inlet and exit were tapered at about 45° to aid streamlined flow. The anolyte and catholyte compartments were separated by a membrane of Nafion ® 425 sulfonated polyether polymer. Spacers provided ⅛" of gap between the membrane and each electrode such that the overall cell gap was ¼". Within each compartment was a mesh of polyethylene with approximately ~¼" square grids and having a thickness of ~⅛" (CONWED XN-5050). The mesh rested against the electrodes, masking each such that the effective area of each electrode was about 40 cm². Each cell compartment was connected by pumps and piping to its own steam heated reservoir. Gaseous 1,3-butadiene was sparged into the anolyte continuously, maintaining a saturated solution of the diene:

EXAMPLE 9

In the above equipment, an anode of Union Carbide WDF graphite felt (~¼" thick) and a cathode of stainless steel were used. An anolyte solution consisting of

| | |
|---|---|
| $Mn(OAc)_2.4H_2O$ | 50 g.(204 mmol) |
| KOAc | 150 g.(1.53 mol) |
| $Cu(OAc)_2.H_2O$ | 14.6 g.(73 mmol) |
| HOAc | 590 ml |
| $Ac_2O$ | 290 ml | and a catholyte consisting of

| | |
|---|---|
| KOAc | 120 g.(1.22 mol) |
| HOAc | 880 ml |
| $Ac_2O$ | 35 ml | were charged into their respective reservoirs. (Ac indicates the acetyl radical, and OAc the acetate anion). The solutions were maintained at ~105° C. and circulated through the cell (anolyte flow rate 1.2 l/min, for a linear rate of 2 l/cm/second; catholyte flow rate 0.5 l/min).

The system was electrolyzed at a constant current of 5 amps (125 ma/cm²) (~12 volts) for three hours. After this time a sample of anolyte was taken, treated with $H_2O$, and silylated with Regisil ® (Regis Chemical). VPC analysis showed a total of 45.7 g of a mixture of 4-acetoxy-5-hexenoic acid and 6-acetoxy-4-hexenoic acid corresponding to a current efficiency of 95%.

55 g. (561 mmol) of KOAc was added to the catholyte and the system was electrolyzed for 3 hours at 5 amps. An anolyte analyzed by VPC as above showed 80.5 g of the mixture of acetoxy acids corresponding to an overall current efficiency of 84%. The anolyte was distilled under reduced pressure to remove most of the acetic acid and acetic anhydride. 200 ml of water was added and the mixture was again distilled to remove most of the liquids. The residue was dissolved in a minimal amount of water and extracted 3× with diethylether. The dried ether solution was distilled under reduced pressure to give 106 g of residue, shown by VPC to contain 79.8 g of a mixture of the acetoxy hexenoic acids. This corresponds to a current efficiency of 83%.

EXAMPLE 10

Example 9 was repeated except electrolysis was continued for a total of thirteen hours. At the end of each three hour period, 55 g of KOAc was added to the anolyte. Results are shown in Table I.

TABLE I

| Hrs. Electrolysis | Grams Acetoxy Hexenoic Acids | Current Efficiency % |
|---|---|---|
| 3 | 42 | 88 |
| 6 | 79 | 82 |
| 9 | 105 | 73 |
| 12 | 123 | 64 |
| 13 | 128 | 62 |

The concentration of trivalent manganese was 18 to 19 millimoles per liter during much of the reaction and 23 millimoles when it was terminated.

EXAMPLE 11

Example 9 was repeated except that
(1) ECL (Union Carbide) flat plate graphite anode was used.
(2) No turbulence promoters were used.

An anolyte flow rate of 3 l/min (linear flow ~34 cm/sec.) was obtained. Area of each electrode was approximately 70 cm². The system was electrolyzed for 48 hr at a constant current of 1 amp (current density ~14 ma/cm²). (4 volts).

KOAc was periodically added to the anolyte similarly to the procedure of examples 9 and 10. Work-up of the anolyte solution gave 84 g. of a mixture of the acetoxyhexenoic acids corresponding to a current efficiency of 58%.

EXAMPLE 12

Example 11 was repeated except that a constant current of 2 amps (~29 ma/cm²) was passed for 17 hr. During the electrolysis an increase in cell voltage from 6 volts to about 15 volts was seen and significant offgassing of $CO_2$ from the anolyte was detected. Work-up of the anolyte gave 25 g of the acetoxy hexenoic acids (current efficiency = 23%).

EXAMPLE 13

Example 12 was repeated with a new ECL graphite anode. Polyethylene mesh (CONWED XN-5050) was used in the flow channels similarly to Example 9. Working area of each electrode was 55 cm². Flow rate of the anolyte was 2.7 l/min (linear flow 47 cm/sec.) A constant current of 1.6 amps (current density 29 ma/cm²) was passed for 30 hr. (6 volts). Work-up of the anolyte gave 109 g of the acetoxy hexenoic acids (71% current efficiency).

EXAMPLE 14

The cell used in Example 13 was modified to give flow channels of 3 cm×15 cm×3.2 mm. The width of the flow channel was gradually tapered to about 1.25 cm wide at the ends to provide streamlined flow. Larger external piping gave a flow rate of 15 l/min (linear flow 404 cm/sec.). Polyethylene mesh turbulence promoters were used, giving a working area of 18 cm² for each electrode. One-half the total quantity of both anolyte and catholyte used in Examples 9–13 was charged to the reservoirs. A constant current of 3 amps (166 ma/cm²) (17 volts) was passed for 5.5 hr. KOAc was added periodically to the anolyte as in previous examples. Results of analyses are given in Table II.

TABLE II

| Hrs. Electrolysis | Grams Acetoxy Hexenoic Acids | Current Efficiency, % |
|---|---|---|
| 3 | 19 | 85 |
| 4.17 | 32 | 79 |
| 5.5 | 40 | 75 |

A divided electrolysis cell is convenient for use for the electrolytic regeneration of trivalent manganese and substantially avoids the problem of butadiene or trivalent manganese reduction at the cathode. Semipermeable membranes can be employed as divider which permit transmission of ions to carry current, e.g. hydrogen or alkali metal ions, or such ions in hydrated form, but substantially prevent transmission of other ions or molecules. Membranes of cation exchange resins are particularly suitable, e.g. those containing sulfonic groups, but anion exchange resins can also be used. The Nafion ® fluoropolymer resin membranes have been found useful, such membranes being composed of fluorinated hydrocarbon resin with pendant ether groups having sulfonic acid substituents. The reaction medium employed in the process is circulated through the anode chamber as anolyte. The catholyte can be electrolyte medium capable of carrying current, but it will generally be desirable to use some components common to the anolyte, such as acetic acid, potassium acetate, acetic anhydride, etc. in order to avoid contamination or dilution of the anolyte by leakage from the catholyte.

Some chemical procedures for preparation of acetoxy hexenoic acids with manganic acetate, with and without co-oxidant, were carried out in accord with the following general procedure.

To a 6 oz. Fisher-Porter bottle is added 20 mmole $Mn(OAc)_3 \cdot 2H_2O$, 10 mmole of desired co-oxidant and 150 ml of 2:1 $AcOH:Ac_2O$. To this is added 110 mmoles or other designated amount of butadiene. A Teflon-coated magnetic stirring bar is added and the bottle sealed. The apparatus is lowered into a constant temperature oil bath heated to 95°–97° C. and the reaction is allowed to continue until the characteristic Mn(III) color is gone. The reaction is allowed to cool to room temperature. The solvent is removed on a rotary evaporator in vacuo at 45° C. until solids remain. $H_2O$ is added and the solids are dissolved. After stirring for several minutes the pH is adjusted to 2 with conc. HCl (pH followed via pH meter). The aqueous layer is then extracted 3 times with diethyl ether. The pH of the aqueous layer is re-examined and if necessary re-adjusted to pH of 2 and re-extracted. The combined ether extracts are dried with anhydrous $MgSO_4$ and the ether is removed in vacuo. A portion of the remaining product is silylated and analyzed via gas chromatography using a Varian 3700 fitted with a 3 mn x 2-meter ov-101/Chromosorb W column. Conditions: 80° to 240° C. at 8°/min, He carrier gas, Tc detector. Ethyl myristate is added as an internal standard. Integration is carried out on an Autolab System IV computer.

The results of procedures using various co-oxidants are shown in the following table.

TABLE III

| Metal Salt (mmoles) | $Mn(OAc)_3$ mmoles | $C_4H_6$ | % Yield[a] |
|---|---|---|---|
| $Cu(OAc)_2$ (10) | 20 | 110 | 85 |
| $Co(OAc)_2$ (5) | 20 | 19 | 57 |
| $Co(OAc)_2$ (10) | 20 | 63 | 47 |
| $Co(OAc)_2$ (20) | 20 | 63 | 44 |
| $Sn(OAc)_2$ (10) | 20 | 72 | 27 |
| $Ni(OAc)_2$ (10) | 20 | 65 | 12 |
| $Fe(OAc)_2$ (10) | 20 | 107 | 15 |
| $Zn(OAc)_2$ (10) | 20 | 112 | 23 |
| $Cr(OAc)_3$ (10) | 20 | 74 | 11 |
| $Ru(acac)_2$[b](0.22) | 20 | 77 | 17 |
| AgOAc (0.6) | 20 | 70 | 26 |
| $Pd(OAc)_2$ (0.5) | 20 | Butene diacetates and many high boilers - Pd | |

[a]Based on Mn(III)
[b]acetyl acetonate

Selectivity was much better with the cupric salt than with any of the other salts tested.

Additional procedures were carried out with various phthalocyanine complexes and other metal compounds as reported in Table IV.

TABLE IV

| Compound (mmoles) | $Mn(OAc)_3$ (mmoles) | $C_4H_6$ (mmoles) | Yield (a) % |
|---|---|---|---|
| Cu(II) phthalocyanine | 20 | 64 | 68 |
| Mn(II) phthalocyanine | 20 | 74 | 17 |
| Co(II)phthalocyanine | 20 | 72 | 27 |
| Zn(II) phthalocyanine | 20 | 52 | 38 |
| Phthalocyanine (tetra- (0.2) sulfonated Na+ salt) | 20 | atm pressure | 32 |
| Ferrocene (0.2) | 20 | 58 | 27 |
| Rubrene (0.2) | 20 | 74 | 72 |
| CuO (solid) (5.3) | 20 | 58 | 45 |
| $CuMn_2O_4$(spinel) (10) | 20 | 17 | 61 |

(a) based on $Mn^{+3}$

When procedures like the above were carried out without a co-oxidant, it was found that the results were affected by the ratio of butadiene to trivalent manganese, with fairly good results possible by controlling such ratio as illustrated in Table V.

TABLE V

| $Mn(OAc)_3$ (mmoles)³ | $C_4H_6$ (mmoles) | Yield of AA % |
|---|---|---|
| 20 | 58 | 27 |
| 20 | 27 | 65 |
| 20 | 12 | 46 |

In Table 6, use of a low concentration of cupric salt is illustrated.

TABLE VI

| Mn(OAc)$_3$ (mmoles) | Cu(OAc)$_2$ (mmoles) | C$_4$H$_6$ (mmoles) | Yield of AA % |
|---|---|---|---|
| 20 | 10 | 110 | 83 |
| 20 | 10 | (a) | 79 |
| 20 | 0.01 | 82 | 76 |

(a) C$_4$H$_6$ continuously bubbled through at atm pressure. Otherwise the same conditions apply.

EXAMPLE 15

A reaction was carried out in a Fisher-Porter bottle as previously described, with 75 ml acetic acid, 25 ml acetic anhydride, 5 grams potassium acetate, 40 millimoles manganic triacetate, 93 millimoles butadiene, and 1 millimole cupric acetate, with heating at 175° C. The reaction was over in 5 minutes and gave an 81% yield of acetoxy hexenoic acids and about a 1.3% yield of γ-vinyl-γ-butyrolactone. Similar results were obtained at higher temperatures from 154° to 210° C., but with somewhat higher yields of lactone in some cases. When a similar reaction was carried out, but omitting the acetic anhydride, the lactone was the primary product. Thus utilizing acetic acid with 10% potassium acetate as solvent and heating butadiene in a ratio of 0.015 mole to 73 ml. of solvent and a stoichiometric amount of manganic acetate dihydrate at a temperature of 160° C. produced a 35% yield of γ-vinyl-γ-butyrolactone. From the gas chromatography retention time it appeared that a 1.6% yield of acetoxyhexenoic acids was also obtained. Similar results were obtained at higher and lower temperatures. When procedures like the above were used, but with substitution of 13 millimoles 1-octene for butadiene, reaction at about 95° C. produced upon isolation 1.78 grams of material identified as dec-3-enoic acid. A similar procedure with 1-butene gave hex-3-enoic acid in good yield. A reaction utilizing a mixture of 49 millimoles butadiene and 23 millimoles 1-butene produced 1.85 grams of product which contained acetoxyhexenoic acids in 62% yield. No product expected from 1-butene was observed.

EXAMPLE 16

3.64 gm V$_2$O$_5$ ($2 \times 10^{-2}$ mole) and 1.0 gm Cu-(OAC)$_2$.H$_2$O ($5 \times 10^{-3}$ mole) were added to 150 ml of 2:1 (V/V) AcOH:Ac$_2$O in a 6 oz Fisher-Porter bottle (magnetic stirrer). To this was added 3.3 gm of butadiene ($6.1 \times 10^{-2}$ mole). Reaction was allowed for 24 hrs at 97° C. The reaction mixture was worked up and analyzed in accord with the general procedure previously described. A 35% yield was obtained based on V(V) present. It is expected that vanadium can be regenerated and utilized in the various procedures described herein illustrating re-generation and re-use of trivalent manganese.

EXAMPLE 17

A cerium (IV) ion was utilized as metal oxidant to produce acetoxyhexenoic acids in a procedure in which the cerium (IV) was electrolytically regenerated. The electrolysis cell was a glass column containing a cylindrical graphite cloth anode with a copper rod cathode in it. Reaction mixture was pumped from a reaction flask through a feed line and up through the column, and then returned to the reaction flask which was kept at 105° C. The anode had a 150 cm$^2$ geometric area, compared to only a 3.2 mm diameter cathode. The approximately 1 liter of reaction mixture was a 2:1 ratio of acetic acid to acetic anhydride with 150 grams potassium acetate and 50 grams Ce(OAc)$_3$. Butadiene was continuously bubbled through the reaction flask to saturate the reaction mixture with butadiene. With a 10 liter per minute flow rate through the electrolysis cell, a 5 ampere current was passed for 2 hours. Isolation of product gave 14.4 grams acetoxyhexenoic acids, for a current selectivity to this product of 45%. Some copper was present in the reaction mixture during the reaction because of the copper cathode.

EXAMPLE 18

An electrolysis cell was constructed of 40 mm. glass tube (internal diameter) with the anode being a piece of $8 \times 20$ cm graphite felt, 6.4 mm thick, fitted against the glass tube forming a cylinder. The cathode was a 3.2 mm copper rod down the center of the cylinder. The geometric anode area was approximately 150 cm$^2$, compared to about 20 cm$^2$ for the cathode. The design was intended to cause a higher cathode potential than anode potential in order to drive the background reaction producing hydrogen from acetic acid and lessen the cathodic reduction of trivalen manganese formed at the anode. The design will also lessen reduction of copper when present in the reaction medium. The cell was used with a plug-flow reactor system in which the reactor was a long reactor coil, a glass tube 25.4 mm internal diameter and 20 feet long with approximately 5.5 liter volume. The reaction medium is pumped up through the electrolysis cell and upon exiting, butadiene is pumped into the medium and it passes through the reactor coil which is heated in an oil bath to about 108° C. The flow rate can be regulated so as to react all the trivalent manganese in the reactor so that only Mn (II) remains for recycle to the electrolysis cell. The reaction mixture from the reactor tube is discharged to a reservoir where unreacted butadiene is swept out by a nitrogen purge in which nitrogen is sparged into the reaction medium from a tube with inlet below the surface and permitted to escape from an outlet located above the surface. Thus the reaction mixture for recycle to the electrolysis cell can be very low in butadiene and have substantially all of its manganese in the divalent state. Reactions were carried out utilizing an electrolyte of 1.5 molar potassium acetate and 0.2 molar Mn(OAc)$_2$.4-H$_2$O in 2:1 (V/V) acetic acid to acetic anhydride. The electrolysis cell temperature was 85° C., the reactor 108°-109° C., and the reservoir 105° C. With a 5.1 ampere current and anode current density of 30 milliamperes/cm$^2$, reactions were carried out as reported in Table VII.

TABLE VII

| Reaction | Flow Rate (ml/min.) | Res. Time (minutes) | Generation Mn (III) (m.mole/min.) | Butadiene Addition (m.mole/min) | Reaction Time (Hrs.) | Current Efficiency (%) |
|---|---|---|---|---|---|---|
| A | 100 | 55 | 3.2 | 3.4 | 2 | 50% |
| B | 280 | 19.6 | 3.2 | 3.4 | 5 | 65% |
| C | 280 | 19.6 | 3.2 | 1.7 | 5 | 33% |

The reported current efficiency is to isolated acetoxyhexenoic acids. The value of 65% for reaction B is comparable to results obtained with chemically generated trivalent manganese, in the absence of copper. Dropping from butadiene equimolar to the generated manganese (III) in reaction B to only slightly over stoichiometric in reaction C caused marked drop in current efficiency in this procedure in which no copper salts as such were added to the electrolyte. The anodes were stable during the reaction and no increase in cell voltage was observed.

EXAMPLE 19

Several reactions were carried out utilizing the electrolysis cell and reactor system described in Example 18. The electrolyte was as previously described except it also contained designated amounts of cupric acetate. The butadiene addition rate was 3.4 millimoles per minute. The current was 5.1 amperes except in reaction G where it was 10.2 amperes. Total reaction time was 5-5.5 hours.

Results are shown in Table VIII.

TABLE VIII

| | $Cu(OAc)_2$ (mmoles) | Anode $(cm^2)$ | Current Density $(ma/cm^2)$ | Flow Rate (ml/min) | Generation Mn(III) (mmol/min) | Reactor Res. Time (minutes) | Current Efficiency (%) |
|---|---|---|---|---|---|---|---|
| D | 1.4 | 157 | 30 | 280 | 3.2 | 19.6 | 92 |
| E | 0.028 | 87 | 60 | 280 | 3.2 | 19.6 | 83 |
| F | 0.0083 | 157 | 30 | 280 | 3.2 | 19.6 | 86 |
| G | 1.7 | 157 | 60 | 500 | 6.4 | 11 | 62 |

The amount of high boiling product, compared to acetoxy hexenoic acids, was very low in all of the reported reactions. The amount of copper deposited on the cathode appeared very small, compared to that which might be obtained with a cathode equal in area to the anode. The reactions indicate that under appropriate conditions reasonably good results can be obtained with an undivided electrolysis cell. The decline in current efficiency under the high current, low residence conditions of reaction G may have been partially due to insufficient butadiene because of the limited solubility at the 105° C. temperature.

EXAMPLE 20

An electrolysis cell was constructed with parallel anode and cathode surfaces separated by a 6.4 mm polypropylene spacer with a large aperture in a direction longitudinal to the flow through the cell. Both electrodes were 5×20 cm in size but the anode had a 6.4 mm carbon felt surface layer, providing a much greater surface area than the metal plate surface layer of the cathode. A glass flask equipped with a condenser served as a reservoir from which the reaction mixture was cycled to the electrolysis cell, and the flask was equipped with an inlet line for sparging butadiene below the surface of the reaction mixture at atmospheric pressure. For the electrolysis, a solution was provided containing 1 liter acetic acid and 0.5 liter acetic anhydride and being 0.2 molar in manganous acetate, 1.5 molar in potassium acetate, and 0.001 molar in cupric acetate. Butadiene was continuously fed as the reactor was stirred with a magnetic stirrer and maintained at 105° C. A 5 ampere current was passed for 4 hours (12 volts cell voltage). Circulation through the cell was about 5 liters/minute. The current was stopped and the reaction mixture allowed to circulate until all the Mn(III) had reacted. From the reaction mixture a 44 gram amount of acetoxyhexenoic acids was separated for a 69% current efficiency. The formation of high boiling product was very low.

While the exemplification of the invention of most immediate interest involves reaction of acetic acid with butadiene to obtain acetoxyhexenoic acids, the invention also includes use of other acids in place of acetic acid. Other acids having at least one replaceable hydrogen atom on the alpha carbon atom react similarly to acetic acid, particularly lower alkanoic acids, such as propionic, butyric, hexanoic acids, etc. Useful acids can be represented by the formula $RCH_2CO_2H$ or $R_2CHCO_2H$, where R is hydrogen or a monovalent organic group, preferably an alkyl group having, for example, 1 to 4 carbon atoms.

Such acids can be oxidized to radicals, $.CHRCO_2H$, e.g., carboxyalkane radicals, and react with butadiene to produce substituted acyloxyhexenoic acids, $RCH_2COOCH_2CH=CHCH_2CHR-COOH$, and

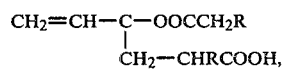

for example 6-acyloxy-2-alkyl-4-hexenoic acids and 4-acyloxy-2-alkyl-5-hexenoic acids. In the event that acids other than acetic are reacted, but acetic acid is also present as solvent, or metal salt, a mixed product may be obtained, depending upon the relative activities of the acids toward the reaction. Thus in the products represented by the above formula, in some cases R would be hydrogen where the reactant was from acetic acid, and in other cases R would be a group from another acid, such as a methyl group from propionic acid. The acyloxy substituent will generally be on a carbon atom other than that of the unsaturated group, usually on a carbon atom adjacent to such group.

If products are desired in which acyloxy groups other than acetic are present on otherwise unsubstituted hexenoic acids, such compounds can be separated from the mixtures. Alternatively, ester exchange reactions can be conducted with acetoxyhexenoic acids, e.g. reacting acetoxyhexenoic acids with propionic acid or its salts or acid chlorides.

Acetoxyhexenoic acids have been found to have effectiveness as antimicrobial agents against various bacteria, particularly nonlactic acid gram positive bacteria, and to a lesser extent against yeasts and molds.

Acetoxyacids were tested for antimicrobial activity against certain food poisoning bacteria. The acetoxyacids employed were a purified mixture of 6-acetoxy-4-hexenoic acid and 4-acetoxy-5-hexenoic acid producted by reaction of butadiene with acetic acid and anhydride in the presence of manganese salts as described herein. The tests were conducted utilizing trypticase soy broth. The growth of specified bacteria was monitored using standard plate count methods daily for three days. The results are reported below in Table IX in the log of the number of cells per ml. The values are approximate, being read from a graph.

TABLE IX

| | Log No. Cells/ml | | | | | | | |
|---|---|---|---|---|---|---|---|---|
| | Staphylococcus Aureus S-6 | | | | Staphylococcus Aureus 12000 | | | |
| | pH 6 | | pH 6.5 | | pH 6 | | pH 6.5 | |
| Additive | 1 day | 3 days | 1 day | 3 days | 1 day | 3 days | 1 day | 3 days |
| Control | 5.7 | 9.2 | 8.8 | 9 | 8.5 | 9.1 | 8.8 | 9.1 |
| 0.1% sorbate | 5.4 | 9 | 8.5 | 8.8 | 5.5 | 8.8 | 8.5 | 8.9 |
| 0.2% sorbate | 4.4 | 8.8 | 8.3 | 8.4 | 3.5 | 8.3 | 8.4 | 8.5 |
| 0.1% AA | 3.9 | 9.1 | 6.7 | 8.7 | 3.7 | 8.6 | 3.6 | 8.8 |
| 0.2% AA | 3.6 | 4.8 | 3.5 | 3.8 | 2.8 | 5.7 | 2.5 | 4 |

*Staphylococcus aureus* FDA 743 was inoculated into Trypticase soy broth and incubated at 30° C. for 24 hours. The bacterium was then inoculated into tubes of the broth of specified pH and preservative combination and incubated at 30° C. The acetoxyhexenoic acids used were comparable to those used above. The optical density at a 600 nanometer setting was then read periodically. The qualitative degree of inhibition, and six-day end points are reported in Table X below.

TABLE X

| | pH 8 | | pH 7 | | pH 6 | |
|---|---|---|---|---|---|---|
| | Inhibition | End Point (O.D.) | Inhibition | End point (O.D.) | Inhibition | End Point (O.D.) |
| Control | — | >4 | — | >6 | — | >6 |
| 0.2% K sorbate | None | >4 | None | >6 | — | — |
| 0.2% acetoxyacid | None | >5 | Virtually complete | 0 | — | — |
| 0.05% K sorbate | — | — | — | — | slight | >3 |
| 0.10% K sorbate | — | — | — | — | slight | >2 |
| 0.05% acetoxyacid | — | — | — | — | moderate* | >2 |
| 0.10% acetoxyacid | — | — | — | — | complete | >0 |

*Initial growth delayed for three days

It can be seen that the acetoxyhexenoic acids were very effective inhibitors at pH's 6 and 7. At a 15° C. incubation temperature, the effect of the agents against *S. aureus* was pH dependent but with the acetoxyhexenoic acids having a broader range of effectiveness than the sorbate, with both potassium sorbate and acetoxyacids at 0.2% concentration showing no effect at pH 8, with the sorbate showing little or no effect at pH 7, while the acetoxyacids gave virtually complete inhibition, and even 0.05% of either agent showing virtually complete inhibition at pH. 6.

Effectiveness against *clostridium perfringens* was tested in Trypticase soy broth at 30° C. by the above procedure and results obtained as reported below in Table XI.

TABLE XI

| | pH 8 | pH 7 | | pH 6 | | pH 5.5 | |
|---|---|---|---|---|---|---|---|
| | End Point (O.D.) | Inhibition | End Point (O.D.) | Inhibition | End Point (O.D.) | Inhibition | End Point (O.D.) |
| Control | .7 | — | >.5 | — | 1.1 | — | >6 |
| 0.2% K sorbate | .6 | None | .6 | — | — | — | — |
| 0.2% acetoxyacid | >.5 | Complete | 0 | — | — | — | — |
| 0.05% K sorbate | — | — | — | moderate | 0.4 | Strong | >0 |
| 0.1% K sorbate | — | — | — | moderate | 0.2 | complete | 0 |
| 0.05% acetoxyacid | — | — | — | moderate | 0.4 | none | >.6 |
| 0.1% acetoxyacid | — | — | — | moderate* | 0.2 | moderate | >.2 |

*Delayed onset of growth 2 days

It is notable that at pH 7 the acetoxyacids were completely inhibitory, while the sorbate was ineffective. At a 15° incubation temperature, 0.2% amounts of the sorbate and acetoxyacids were slightly effective at pH 8.0 against *C. perfringens* with the sorbate being somewhat the better, while at pH 7.0 the sorbate was only slightly effective while the acetoxyacids gave complete inhibition. At pH 6.0, neither was effective at 0.05% amounts, while both gave virtually complete inhibition at 0.1%.

At 30° C. 0.2% of acetoxyacids completely inhibits growth of *Bacillus cereus* in pH 8.0 broth compared to no effect for sorbate, but only slightly reduces growth at pH 7.0; at pH 6.0 0.1% is very inhibitory while 0.1% sorbate is only slightly inhibitory. No growth occurred below pH 6.0. At 15° C., 0.2% acetoxyacid was almost completely inhibitory at pH 8.0 and pH 7.0, being much better than sorbate which was only slightly inhibitory; at pH 6.0 and below no growth occurred in the presence of the preservatives.

It can be concluded that acetoxyhexenoic acids possess strong antimicrobial activity against gram positive bacteria which is generally greater than that of sorbic acid, and that the activity generally extends up to pH 7, and in some cases higher. This is significant as many foods to be preserved have pH's in the range of 5 to 6.5, and the acetoxyhexenoic acids appear more than sufficiently inhibitory in such ranges.

In the antimicrobial comparisons herein, sorbic acid is generally used in the form of its potassium salt in order to have water solubility because of the aqueous broth employed in the tests, while the acetoxyhexanoic acids can be used in acid form as the solubility is sufficient.

The acetoxyhexenoic acids were generally not as effective against yeasts and molds as sorbic acid, although acetoxyhexenoic acids at 0.2% was somewhat more effective than sorbate at 15° against *C. albicans,* and was effective to some extent against *Penicillium italicum* and *Fusarium roseum* at low pH's.

Against Salmonella at 30° C. 0.20% acetoxyacids was very slightly effective at pH 8.0, moderately effective at pH 7.0, and strongly effective at pH 6.0. The compound was moderately to slightly effective at pH's 5.5 and 5.0, with a 0.10% concentration being better than 0.20%. Potassium sorbate gave similar results at pH 6.0 but better results at pH 5.5 and pH 5.0, although the acetoxyacids delayed onset of growth at pH's 6.0 and 5.5.

At 15° C., acetoxyacids gave some inhibition of growth of Salmonella in 7-day tests over pH's from 8.0 to 5.5, and delayed onset of growth compared to potassium sorbate, although later growth was rapid. At pH 6.0 a 0.2% concentration of acetoxyacids was strongly inhibitory over the seven-day test, as was 0.10% acetoxyacid at pH 5.5.

With regard to gram negative bacteria, results indicate that in general acetoxy acid and potassium sorbate are comparable in effect against growth of the bacteria, with the acetoxyacid generally being more effective above pH 6.0, while the sorbate is generally more effective as the pH drops.

The acyloxyhexenoic acids in general as described herein are expected to exhibit antimicrobial properties similar to those of the 6- and 4-acetoxyhexenoic acids used as exemplifications herein.

Procedures are described herein for recovering acyloxyhexenoic acids from reaction media, and distillation, crystallization, or other known procedures can be employed for further refining the acyloxyhexenoic acid products. For use as a food preservative and in similar applications, a high degree of purity is desirable. Aside from the possibly deleterious effects of contaminants, food grade materials may be required to meet certain specification and uniformity standards to fulfill regulatory requirements.

As one might conclude from the description of the present invention, it is possible to convert it to a process for producing $\gamma$-vinyl-$\gamma$-butyrolactone, such as by not utilizing acetic anhydride and running the process in the presence of small amounts of water. In such event the various factors described herein for effective electrolytic regeneration of metal ion oxidants will then be useful in a process for producing lactone. However, the present process is concerned with production of acetoxyhexenoic acids and conditions will generally be employed to produce that as the predominant product of the acetic acid reaction with butadiene, often with selectivities to acetoxyhexenoic acids well above 50%, such as over 70 or 80%.

What is claimed is:

1. A process for preparing acyloxy-alkanoic acids which comprises reacting lower alkanoic acid having at least one replaceable hydrogen atom on the alpha carbon atom and butadiene in the presence of lower alkanoic acid anhydride and one or more metal oxidants in a valence higher than its lowest positive valence and selected from manganese, vanadium and cerium at an elevated temperature to produce such acyloxyhexenoic acids, utilizing the metal ion oxidant in an amount less than stoichiometric with respect to butadiene and repeatedly electrolytically regenerating and utilizing the higher valent state of the ion during the course of the reaction.

2. A process of preparing acetoxyhexenoic acids in which butadiene and acetic acid are reacted in the presence of copper and trivalent manganese ions, and in which the manganese and copper in the reaction mixture repeatedly go through an oxidation-reduction cycle with electrolysis being used for oxidation.

3. A process of preparing and recovering acetoxyhexenoic acids which comprises reacting butadiene and acetic acid in the presence of copper and trivalent manganese ions, employing manganese in amounts less than stoichiometric with respect to butadiene, and electrolytically regenerating trivalent manganese in the reaction mixture during the process for further use therein, with the copper ions also going through oxidation-reduction cycles during the process and facilitating production of acetoxyhexenoic acids, and effecting separation between the acetoxyacid products and manganese and copper components.

4. The process of claim 1 in which temperature is controlled to a value no greater than about 140° C. during the reaction.

5. The process of claim 1 in which temperature during the reaction is maintained within the range of about 80° C. to about 120° C.

6. The process of claim 1 in which manganese ion is present as a metal ion oxidant.

7. The process of claim 1 in which the alkanoic acid is acetic acid and acetic anhydride is present in amount in the range of about 0.2 mole to about 0.8 mole per mole of acetic acid.

8. The process of claim 7 in which a porous carbon anode is used for the electrolytic regeneration.

9. The process of claim 1 in which both a carbon anode and a carbon cathode are in contact with the reaction mixture during the electrolysis.

10. The process of claim 7 in which the butadiene concentration in the reactor is in the range of about 0.05 to about 0.3 mole per liter and trivalent manganese is the metal oxidant.

11. The process of claim 7 in which electrolysis is conducted with an anode having at least 10 times larger area than the cathode and sufficient current being used that the current density at the cathode is very high and sufficient to cause a strong negative potential at the cathode, thereby promoting hydrogen production and lessening the tendency for butadiene reduction.

12. The process of claim 2 in which the butadiene concentration is greater than about 0.25 mole/liter.

13. The process of claim 2 in which the butadiene concentration is greater than about 1 mole/liter.

14. The process of claim 2 in which the butadiene concentration is in the range of about 0.05 to about 5 moles/liter.

15. The process of claim 1 in which potassium acetate is present as electrolyte.

16. The process of claim 2 in which a carbon anode is utilized.

17. The process of claim 2 in which a high surface area anode is used characterized as having surface area more than 100 times that calculated from its bulk geometric dimensions.

18. The process of claim 2 in which a carbon fiber anode is used.

19. The process of claim 2 in which acetic anhydride is present and the process is operated with a carbon anode and continuous addition of reactants utilizing current densities at the anode in excess of 100 milliamperes per square centimeter with a reaction at a rate to provide more than 0.1 gram moles acetoxyhexenoic acids per liter-hour.

20. The process of claim 19 in which manganese is present in the range of about 10 to about 300 millimoles per liter and trivalent manganese in the range of about 10 to about 50 millimoles per liter, and butadiene in amounts from about 3 to about 10 times that of the trivalent manganese on a molar basis, and mass transfer and conditions are such as to provide high current efficiency to desired product.

21. The process of claim 1 in which the electrolytic regeneration is effected in a divided electrolysis cell with the anode and cathode separated by a semipermeable membrane.

22. The process of claim 21 in which an ion exchange membrane is used.

23. The process of claim 21 in which the membrane is a fluorinated hydrocarbon polymer with pendant ether groups having sulfonic substitution such as Nafion ® 425.

24. The process of claim 20 in which the reaction medium is rapidly cycled through an electrolysis cell of much smaller volume than the reaction medium at a rate to pass the entire reaction medium through the cell many times during the reaction in order to allow regeneration of trivalent manganese and increased concentration of product.

25. The process of claim 1 in which the tetravalent cerium is the metal oxidant.

26. The process of claim 1 in which pentavalent vanadium is the metal oxidant.

27. A process for preparing acetoxyhexenoic acids which comprises reacting acetic acid, acetic anhydride and butadiene in the presence of trivalent manganese under conditions to produce such acetoxyhexenoic acids with selectivity of butadiene reactant to such acids of at least 70%, utilizing manganese in an amount less than stoichiometric with respect to butadiene and repeatedly electrolytically regenerating and utilizing the trivalent state of the manganese during the course of the reaction.

* * * * *